United States Patent
Grimm et al.

(10) Patent No.: US 8,758,307 B2
(45) Date of Patent: Jun. 24, 2014

(54) SELF-PRIMING, ANTI-FREE FLOW VALVE FOR INFUSION PUMPS

(75) Inventors: John D. Grimm, Schnecksville, PA (US); Joel M. Bartholomew, Danielsville, PA (US); Kenneth C. Raines, Bethlehem, PA (US); Martin Unverdorben, Pottstown, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 0 days.

(21) Appl. No.: 13/524,520

(22) Filed: Jun. 15, 2012

(65) Prior Publication Data

US 2013/0338588 A1 Dec. 19, 2013

(51) Int. Cl.
*A61M 39/00* (2006.01)

(52) U.S. Cl.
USPC ............................................................. 604/247

(58) Field of Classification Search
USPC .......................................... 604/246, 247, 256
See application file for complete search history.

(56) References Cited

U.S. PATENT DOCUMENTS

| | | |
|---|---|---|
| 5,954,696 A | 9/1999 | Ryan |
| 6,092,551 A | 7/2000 | Bennett |
| 2007/0017583 A1 * | 1/2007 | Fangrow, Jr. ............. 137/614.06 |
| 2007/0156118 A1 * | 7/2007 | Ramsey et al. ............... 604/533 |
| 2008/0287920 A1 * | 11/2008 | Fangrow et al. ............. 604/535 |
| 2010/0063445 A1 | 3/2010 | Sternberg et al. |
| 2011/0276031 A1 | 11/2011 | Hoang et al. |

FOREIGN PATENT DOCUMENTS

| | | |
|---|---|---|
| EP | 0 081 655 A1 | 6/1983 |
| EP | 2 153 865 A2 | 2/2010 |
| WO | WO 99/13937 | 3/1999 |

OTHER PUBLICATIONS

International Search Report and Written Opinion issued in corresponding International Application No. PCT/US2013/042998, mailed Aug. 6, 2013.

* cited by examiner

*Primary Examiner* — Aarti B Berdichevsky
(74) *Attorney, Agent, or Firm* — RatnerPrestia

(57) ABSTRACT

A self-priming IV set valve includes a connector including a valve element that is positioned inside of the connector, and a cap that is removably connected to the connector. When the cap is mounted to the connector a passageway is formed in the connector such that air and liquid are permitted to pass through the connector and into the cap whereupon a hydrophobic filter of the cap prevents the passage of liquid there through while the hydrophobic filter permits the passage of air out of the cap and into the atmosphere. When the cap is not mounted to the connector, the valve element of the connector is configured to open under pressure and close when pressure ceases. Also disclosed is a method of priming the IV set, a cap assembly for a self-priming IV set valve, and a connector for a self-priming IV set valve.

17 Claims, 7 Drawing Sheets

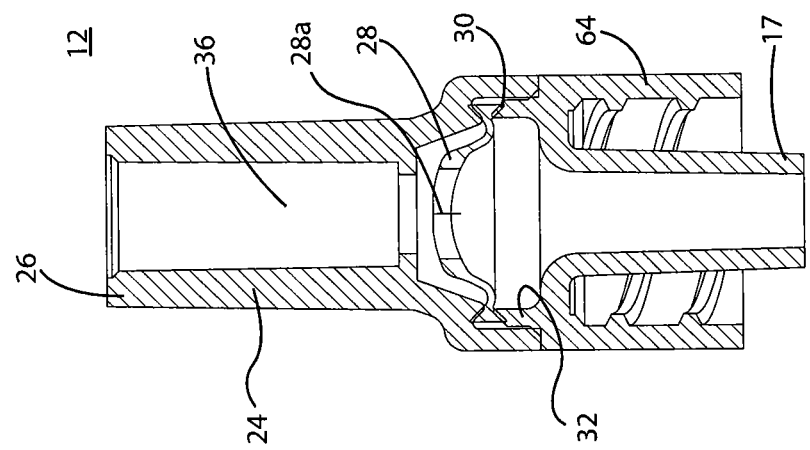
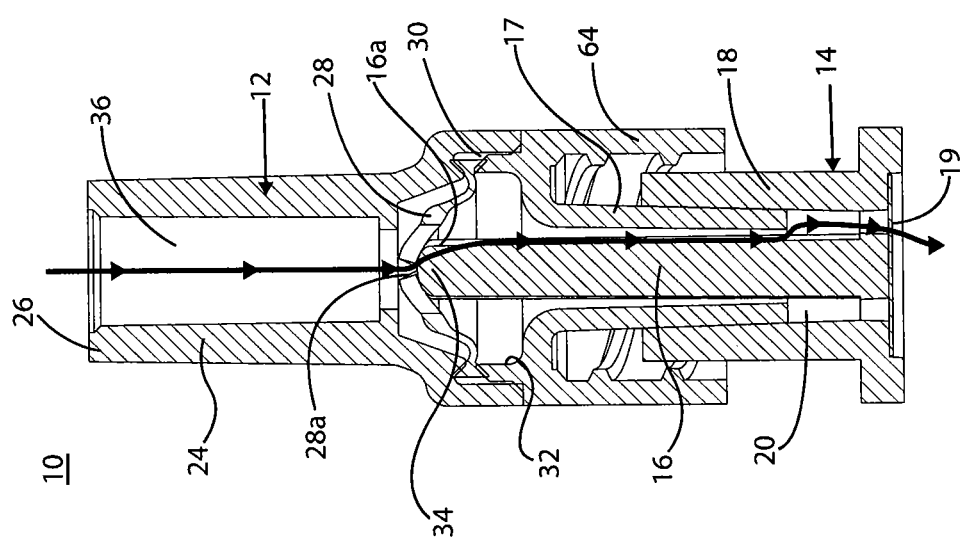
FIG. 1A
FIG. 1B

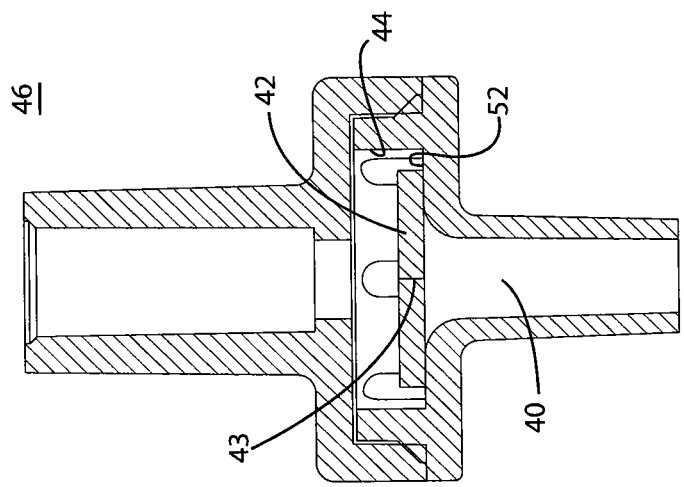
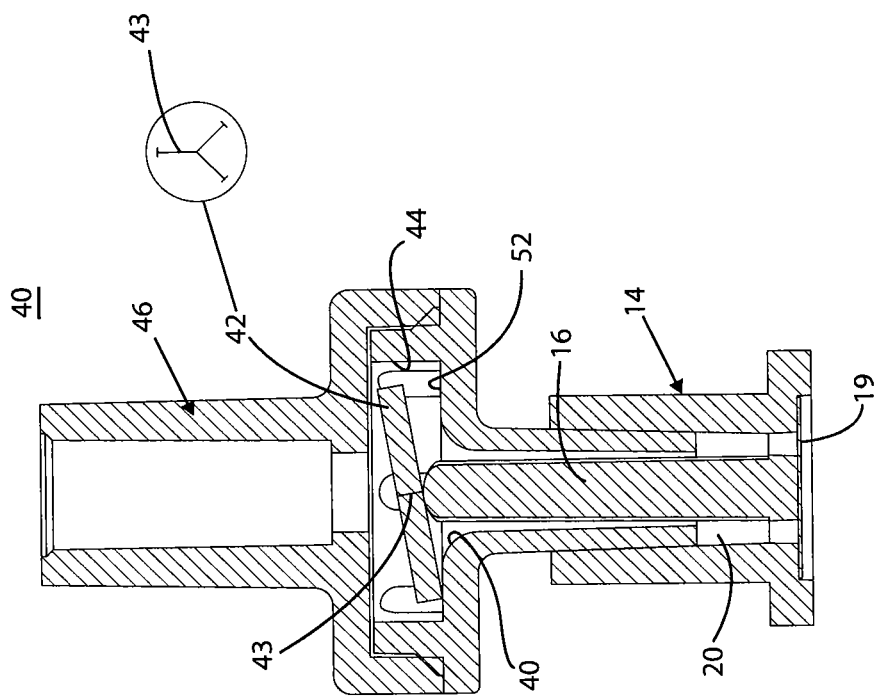
FIG. 2A
FIG. 2B

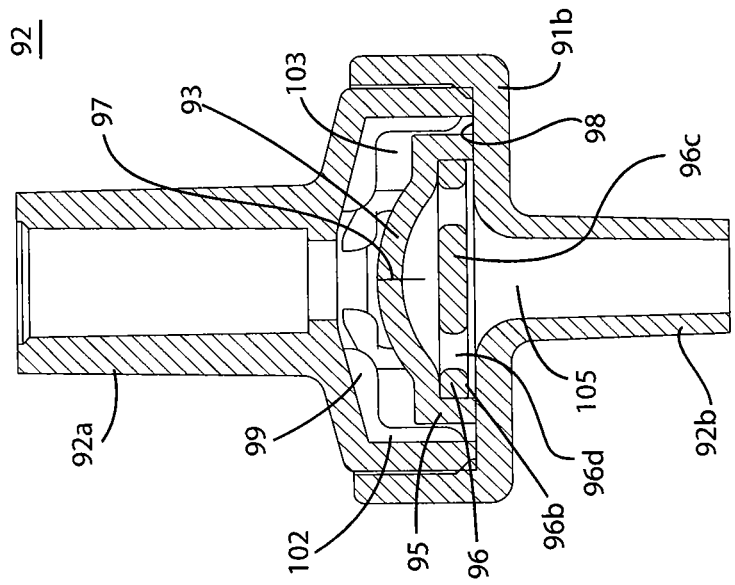
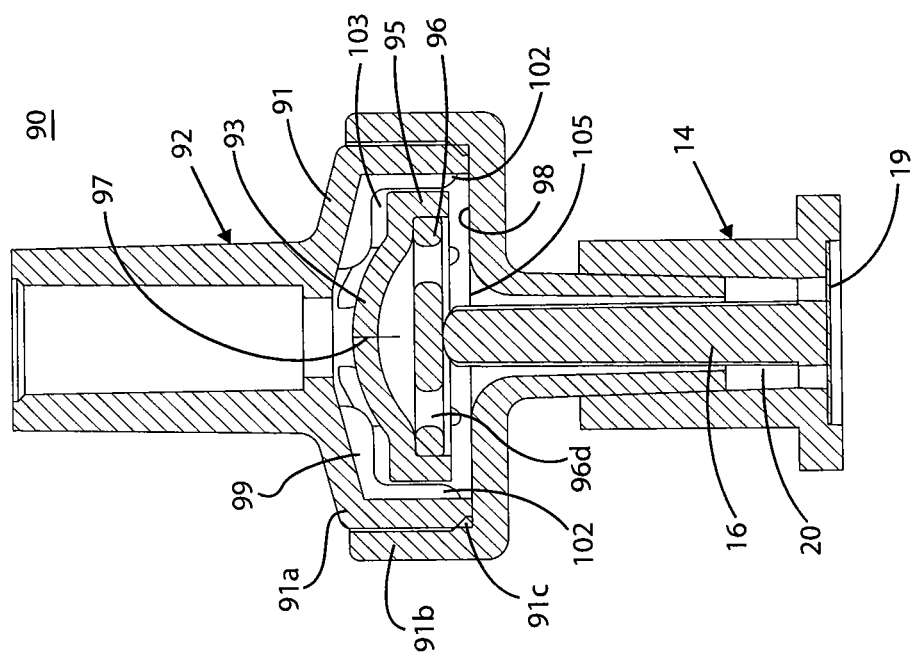
FIG. 4A
FIG. 4B

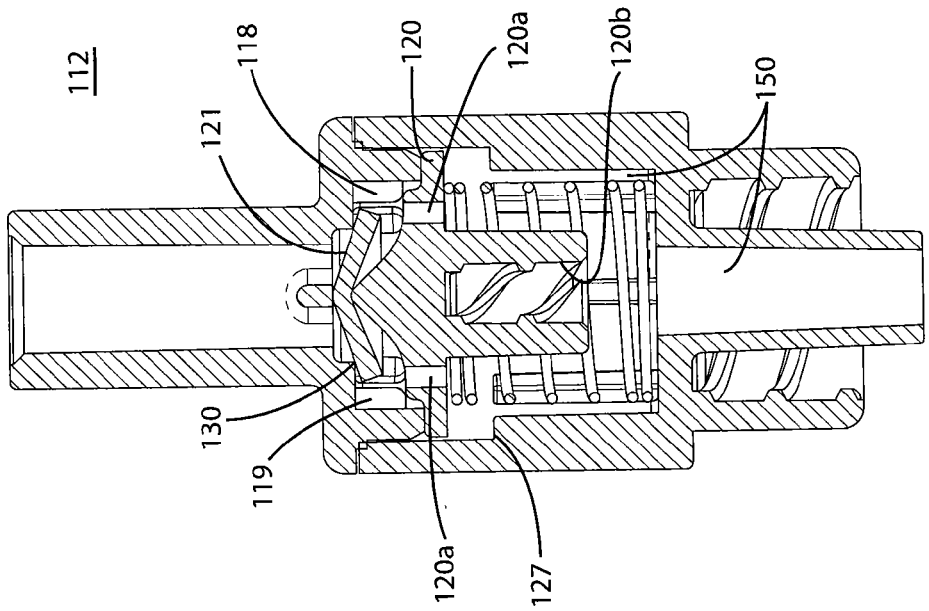
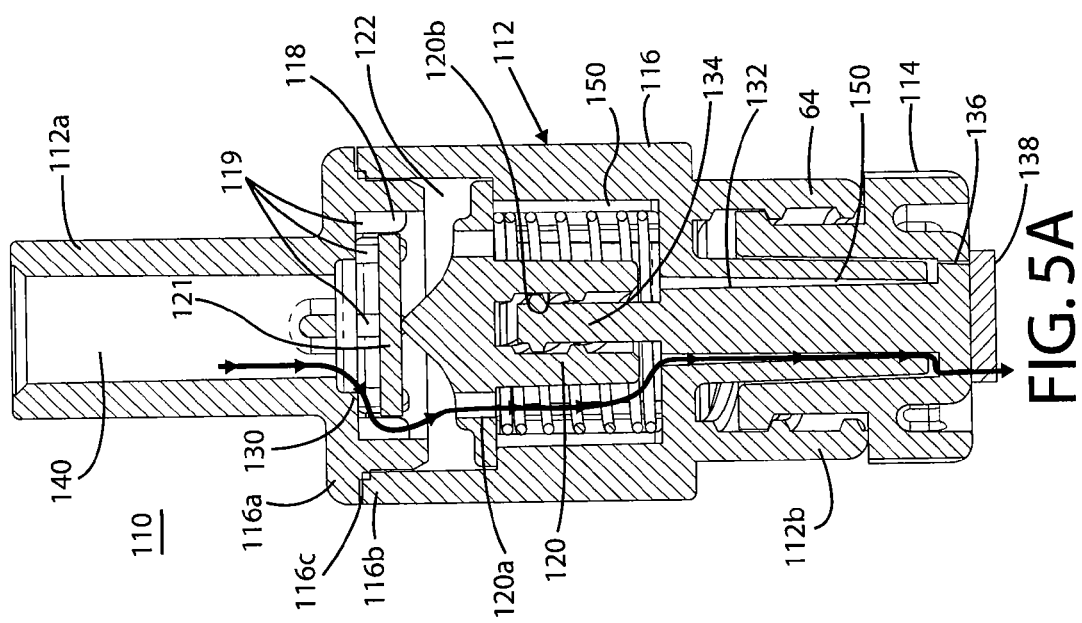
FIG. 5B
FIG. 5A

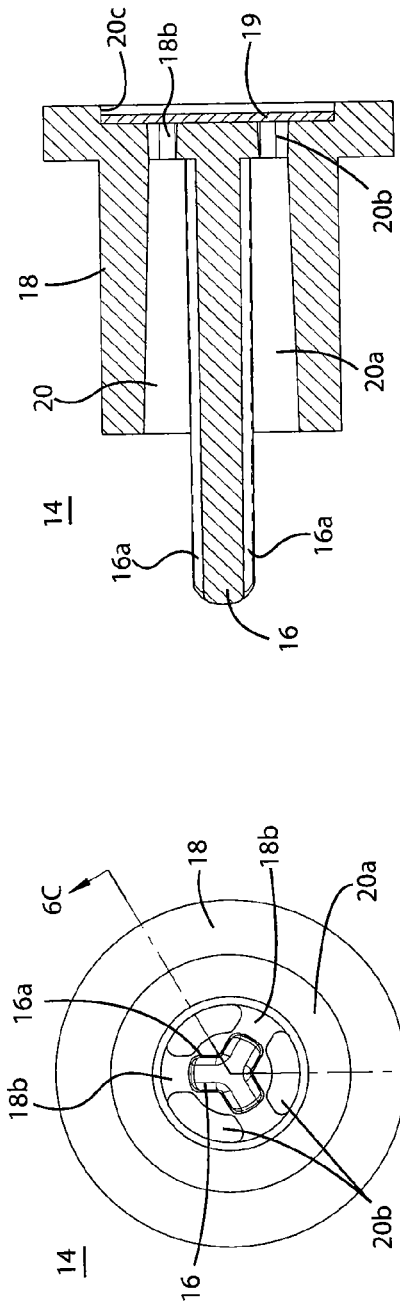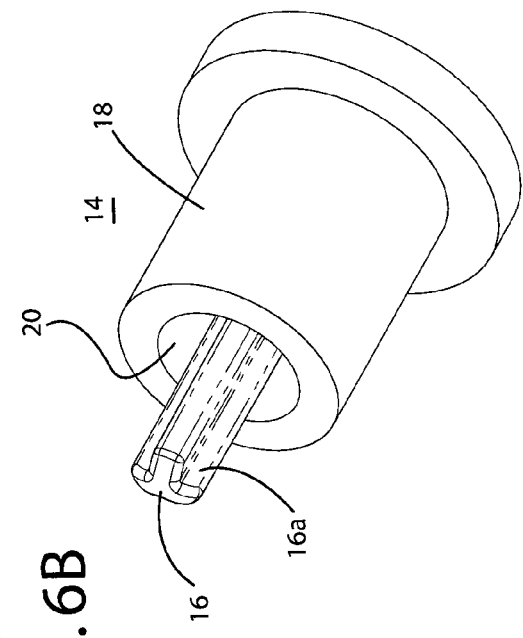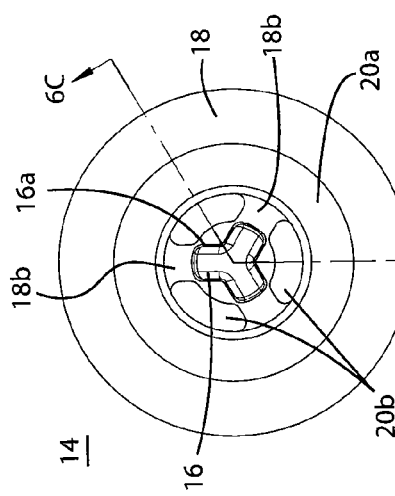
FIG. 6C
FIG. 6A
FIG. 6B

SELF-PRIMING, ANTI-FREE FLOW VALVE FOR INFUSION PUMPS

FIELD OF THE INVENTION

This invention relates to a medical valve for an IV set.

BACKGROUND OF THE INVENTION

As disclosed in U.S. Pat. No. 5,954,696 to Ryan, which is incorporated by reference herein in its entirety, an infusion intravenous (IV) set can be used with an ambulatory infusion pump to deliver fluid from an IV bag within the infusion pump to a patient. Though termed an "IV set," the set may be used for any type of vascular infusion.

Conventional infusion sets comprise clear, flexible medical grade tubing, terminating at one end in a bag spike, and terminating at the other end in a conventional Luer, or any other type of medical connector. A releasable clamp is positioned along the length of the tubing to prevent the inadvertent passage of fluid through the tubing.

In use, intravenous (IV) infusion sets are typically primed with fluid prior to use to ensure that all air has been removed from inside the tubing that is attached to the IV bag. The spiking and priming process typically involves first closing a clamp that is mounted to the tubing and then spiking an IV bag with a bag spike or any other connector that is attached to a proximal end of the tubing. The IV bag is then hung from a pole and the operator opens the clamp. The fluid then travels through length of the tubing under gravity and travels beyond the open clamp. When reaching the distal end of the tubing, the operator closes the clamp to stop the fluid. If the clamp is not completely closed, then fluid may drip from the distal end of the tubing.

SUMMARY OF THE INVENTION

This invention (1) simplifies the process of priming the infusion set in an effort to save time especially if a number of bags need to be set-up, (2) either reduces or eliminates the fluid discharge from the end of the IV set during priming, (3) provides an anti-siphon feature to prevent runaway of fluid if the tubing clamp is not closed or the IV set is removed or dislodged from the pumping mechanism in situations where the set is used in infusion pumps.

According to one aspect of the invention, a self-priming IV set valve includes a connector (such as a Luer connector) and a valve element positioned within the connector. A proximal end of the connector is connectable to the infusion set and a distal end of the connector is connectable to a catheter or any other infusion line. A cap is mounted to the distal end of the connector creating a fluid passageway within the valve through which air and liquid can pass into the cap and onto a hydrophobic filter of the cap. The hydrophobic filter prevents the passage of liquid there-through while the hydrophobic filter permits the passage of air out of the cap and into the atmosphere. When the cap is not mounted to the connector, the valve element within the connector is configured to open under pump pressure and close when pump pressure ceases.

According to another aspect of the invention, a method of priming an IV set comprises the steps of connecting the cap to the connector thereby exposing a fluid passageway between the connector and the cap; delivering fluid including air and liquid through the tubing, into the connector, through the fluid passageway, into the cap and onto a hydrophobic filter of the cap thereby preventing the passage of liquid through the hydrophobic filter while permitting the passage of air out of the cap and into the atmosphere.

According to yet another aspect of the invention, a cap assembly for a self-priming IV set valve comprises a body portion that is configured to be removably connected to the IV set valve. An actuator has a fixed end that is mounted to the body portion and a free end that is configured to either puncture, move or displace a valve element of the IV set valve. A hydrophobic filter is mounted to the actuator. A chamber is disposed in the body portion between the free end of the actuator and the hydrophobic filter. When the cap assembly is mounted to the IV set valve, the hollow actuator tube either punctures, moves or displaces the valve element of the IV set valve such that air and liquid within the IV set valve can flow at least partially through the actuator and into the chamber of the cap assembly, whereupon the hydrophobic filter of the cap assembly prevents the passage of liquid through the hydrophobic filter while the hydrophobic filter permits the passage of air there-through and into the atmosphere.

According to yet another aspect of the invention, a connector of a self-priming IV set valve comprises a connector body including a hollow region; and a valve element that is at least partially positioned in the hollow region that is configured to be either moved or punctured by a cap that is releasably connectable to the connector body. When the cap is mounted to the connector, the cap either punctures or moves the valve element and a passageway is formed in the connector such that air and liquid are permitted to pass through the connector and into the cap. When the cap is not mounted to the connector, the valve element of the connector is configured to open under pressure to permit the passage of liquid through the connector and close when pressure ceases.

BRIEF DESCRIPTION OF THE DRAWING FIGURES

The invention is best understood from the following detailed description when read in connection with the accompanying drawing. Included in the drawing are the following figures:

FIG. 1A depicts a cross-sectional side elevation view of an IV set valve including a vented end cap assembly that is releasably mounted to a connector according to a first exemplary embodiment of the invention, and FIG. 1B depicts the connector of FIG. 1A without the vented end cap assembly.

FIG. 2A depicts a cross-sectional side elevation view of another IV set valve according to a second exemplary embodiment of the invention, and FIG. 2B depicts the connector of FIG. 2A without the vented end cap assembly.

FIG. 4A depicts a cross-sectional side elevation view of still another IV set valve according to a fourth exemplary embodiment of the invention, and FIG. 4B depicts the connector of FIG. 4A without the vented end cap assembly.

FIG. 5A depicts a cross-sectional side elevation view of still another IV set valve according to a fifth exemplary embodiment of the invention, and FIG. 5B depicts the connector of FIG. 5A without the vented end cap assembly.

FIG. 6A depicts a perspective view of the cap assembly of FIGS. 1A, 2A, 3A and 4A.

FIG. 6B depicts a top plan view of the cap assembly of FIG. 6A.

FIG. 6C depicts a cross-sectional view of the cap assembly of FIG. 6B taken along the lines 6C-6C.

DETAILED DESCRIPTION OF THE DRAWING FIGURES

Figure 3B:
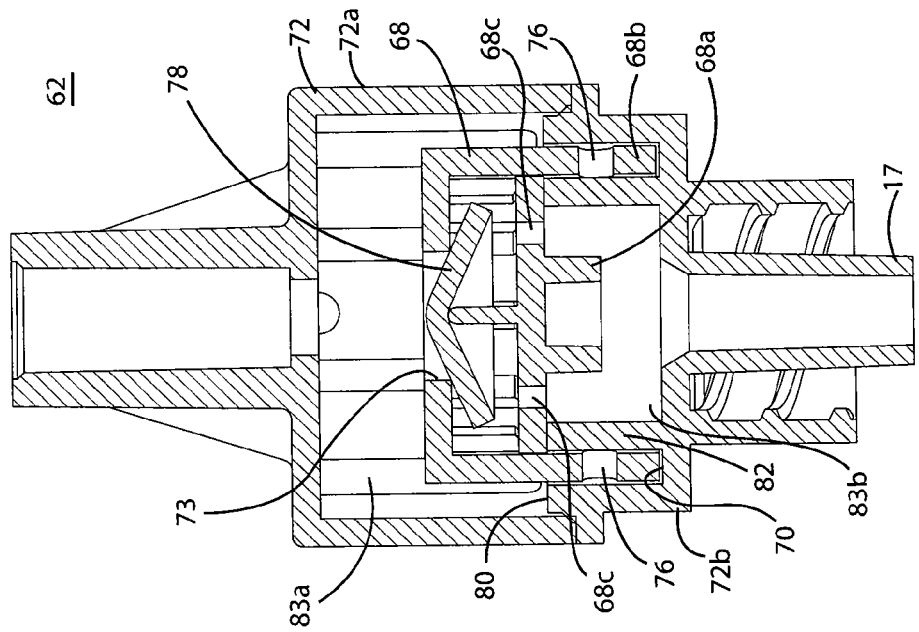
FIG. 3B depicts the connector of FIG. 3A without the vented end cap assembly.

The invention is best understood from the following detailed description when read in connection with the accompanying drawing figures, which shows exemplary embodiments of the invention selected for illustrative purposes. The invention will be illustrated with reference to the figures. Such figures are intended to be illustrative rather than limiting and are included herewith to facilitate the explanation of the present invention.

As used herein, the term 'underinfusion' generally refers to infusion of fluid into a patient at a rate lower than intended.

As used herein, the term 'overinfusion' generally refers to infusion of fluid into a patient at a rate higher than intended.

As used herein, the term 'uncontrolled flow' refers to the flow of fluid through the set without control, e.g., according to the law of physics.

As used herein, the term 'freeflow' generally refers to uncontrolled flow through a set that is connected to the patient. Freeflow encompasses underinfusion and overinfusion while correct flow under freeflow condition is unlikely.

As used herein, the term 'self-priming' generally refers to venting of the set that does not require any interference from either a person or a machine.

As used herein, the term 'pump priming' generally refers to venting of the set under control of an infusion pump after being inserted into the latter.

As used herein, the term 'anti-freeflow' generally refers to any measure that prevents or stops freeflow.

Turning now to FIG. 6 of U.S. Pat. No. 5,954,696 to Ryan, an infusion set, indicated generally at 80, is adapted for use with the ambulatory infusion pump. As illustrated in FIG. 6 of the '696 Patent, the infusion set 80 generally comprises clear, flexible, medical grade tubing 82. A bag spike 22 is mounted at a proximal end (i.e., proximal to the IV bag) of the tubing 82 and a conventional Luer-type medical connector 84 is mounted at a distal end of the tubing 82. A check valve 86 is mounted to the tubing 82 to prevent "flashback" when, for example, the infusion pump is turned-off, the cover opened, and the system depressurizes. An air eliminating filter 88 of a type well understood in the art and a flow controlling resistive lumen or orifice 101, positioned immediately upstream to the Luer fitting 84, are also mounted to the tubing 82.

Referring generally to the Figures, the five inventive IV set valves described hereinafter may be used as a substitute for Ryan's Luer-type medical connector 84 that is mounted at the distal end of the IV set tubing 82, as shown in FIG. 6 of the '696 Patent. Each IV set valve embodiment disclosed herein includes a connector (such as a Luer connector) and a vented cap that is releasably mounted to the connector. The vented cap may have a hydrophobic filter to allow air to be purged from the IV set but not fluid. Mounting the cap to the connector creates a fluid passageway between the cap and the connector to allow air and fluid to pass into the cap during an air purge. Removing the cap from the connector closes the fluid passageway, thereby preventing fluid from exiting the IV set. A valve element that is positioned inside the connector is designed to open under pump pressure and close when pressure ceases. In the event that the IV set is removed from the pump or dislodged from the pumping mechanism by an open door, etc., flow through the valve element will not be possible if the cap is removed (i.e., no gravity flow will be possible).

Referring now the first embodiment of the IV set valve 10 shown in FIG. 1A, the IV set valve 10 includes a connector 12 and a vented end cap assembly 14 that is releasably mounted to the connector 12. The IV set valve 10 may or may not be permanently mounted to an IV set (not shown). The vented cap assembly 14 is shown mounted to the connector 12 in FIG. 1A, and the vented cap assembly 14 is shown removed from the connector 12 in FIG. 1B. As will be described later, the vented cap assembly 14 may also be used with other connectors that are shown herein.

According to one aspect of the invention, the connector 12 of the IV set valve 10 is a male Luer connector, however, it should be understood that the connector 12 is not limited to being either a Luer connector or a male Luer connector, as other types of medical connectors are envisioned.

Turning now to the features of the male Luer connector 12, the male Luer connector 12 generally includes a two-piece hollow body 24 and a valve element 28 that is non-removably mounted at the interface 30 of the two pieces of the connector 12. The pieces of the hollow body 24 are fixed to each other at interface 30 by either an adhesive or an ultrasonic weld, for example.

The top piece of the hollow body 24 includes a tubular shaped proximal end 26 defining a fluid passageway. The tubular shaped proximal end 26 has a hollow chamber 36 in which fluid from the IV bag can collect. The bottom piece of the hollow body 24 is a Luer connector comprising a frusto-conical portion 17 defining a fluid passageway, and a shroud 64 having internal female threads that surrounds the frusto-conical portion 17. The female threads of the shroud 64 are configured for coupling with mating threads of either the end cap assembly 14 (as shown in FIG. 1A) or a female Luer connector (not shown).

The valve element 28 of the connector 12 is biased toward a closed position (as shown in FIG. 1B). In the absence of pressure or the actuator 16 of the cap assembly 14, the valve element 28 prevents the passage of gases and liquid there through. In the presence of either the actuator 16 (as shown in FIG. 1A) or pressurized fluid produced by either gravity or an infusion pump, the valve element 28 opens to permit the passage of gases and liquid there through. The valve element 28 is also configured to prevent siphoning of fluid from the IV bag. The valve element 28 may also be referred to herein as a valve, a valve element, or a seal.

FIGS. 6A-6C depict the vented end cap assembly 14 that is configured to be releasably connected to the connectors 12, 46, 62 and 92 of FIGS. 1B, 2B, 3B and 4B, respectively. The vented end cap assembly 14 may or may not be pre-mounted onto the distal end of the connector 12. Referring now to the components of the vented end cap assembly 14, the assembly 14 generally includes a body portion 18 defining an annular fluid passageway 20, and a hydrophobic filter 19 that is mounted to the base end of the body portion 18. Fluid passageway 20 may also be referred to herein as a fluid chamber.

The body portion 18 includes an actuator 16 that extends upwardly from the base end of the body portion 18. The actuator 16 has a three point star shape in cross-section. A series of three recessed semi-circular regions 16a are evenly distributed about the circumference of the actuator 16. Each region 16a extends from the tip at the free end 34 of the actuator 16 to the fixed end of the actuator 16. Each recessed region 16a extends the length of the actuator 16. As will be described later, the recessed regions 16a form part of the fluid passageway of the vented end cap assembly 14.

The fluid passageway 20 of the end cap assembly 14 has three passageway portions 20a-20c. The annular portion 20a of the fluid passageway 20 is sized to at least partially receive the frustoconical end 17 of the male Luer connector 12. The passageway portion 20b comprises a series of openings that are defined between ribs 18b of the body portion 18 (see FIG. 6B). The portion 22c of the fluid passageway 20 is sized to receive the hydrophobic filter vent 19.

The hydrophobic filter vent 19 is especially configured to allow the passage of air there through, while at the same time substantially preventing or limiting the passage of liquid there through. The hydrophobic filter vent 19 may be composed of a hydrophobic porous material such as Teflon, Polysulfone or glass fiber media. Such filters are distributed by the Pall Corporation of Port Washington, N.Y., USA.

The body portion 18 of the cap assembly 14 may be composed of either a plastic or a metallic material. The body portion 18 may be formed by injection molding or die casting, for example. The body portion 18 may or may not be coated with a hydrophobic substance and or an antimicrobial compound.

To prime an IV set including the valve 10, one end of an IV set is connected to the proximal end 26 of the valve 10, and the other end of the IV set is fluidly connected to an IV bag (not shown). The end cap assembly 14 is fitted onto the distal end of the male Luer connector 12 of the valve 10 for self-priming purposes. As the end cap assembly 14 is fitted onto the male Luer connector 12, the top end 34 of the actuator 16 penetrates the opening 28a (see FIG. 1A) of the valve 28.

By the force of gravity, fluid flows from the IV bag and into the IV set. The fluid within the IV set travels through the tubing of the IV set, and into the chamber 36 of the male Luer connector 12. As shown by the arrows in FIG. 1A, any air within the tubing is also urged through the tube and into the chamber 36 of the male Luer connector 12. The liquid and air within the chamber 36 then travel through the valve opening 28a, down and along the recessed regions 16a of the actuator 16, and into the fluid passageway 20 of the cap assembly 14 that is delimited by the hydrophobic filter vent 19. The fluid then collects on the hydrophobic filter vent 19. The air passes through the hydrophobic filter vent 19, while the liquid remains in the passageway 20 on top of the hydrophobic filter vent 19. At this point, the IV set is self-primed and free of air.

Once the air is purged from the IV set, the cap assembly 14 is removed from the male Luer connector 12. The valve 28 returns to a closed position once the actuator 16 is removed from the Luer connector 12. The distal end of the male Luer connector 12 is then either directly or indirectly connected to a catheter that is connected to a patient's vascular system. The liquid from the IV bag is then delivered under pressure through the IV set by an infusion pump that is connected to the IV set. The pressurized liquid opens the opening 28a of the valve 28, and the liquid is expelled from the male Luer connector 12 and is ultimately distributed intravenously to the patient by the catheter.

FIG. 2A depicts a cross-sectional side elevation view of another IV set valve 40 according to a second exemplary embodiment of the invention. The IV set valve 40 generally includes a male Luer connector 46 (shown by itself in FIG. 2B) and the previously-described end cap assembly 14. The IV set valve 40 is substantially similar to the set valve 10 of FIG. 1, and only the primary differences between those valves will be described hereinafter.

The IV set valve 40 includes a slit disc 42. The slit disc 42 may also be referred to herein as a valve, a valve element, or a seal. As best shown in the detailed view to the right of FIG. 2, the slit disc 42 includes normally-closed radial slits 43 that open to permit the passage of pressurized liquid. The slit disc 42 is moveably positioned in an enlarged chamber 44 of the male Luer lock connector 46.

To prime an IV set including the valve 40, the IV set is fluidly connected to the IV bag (not shown). The end cap assembly 14 is fitted onto the male Luer connector 46. As the end cap assembly 14 is fitted onto the male Luer connector 46, the actuator 16 pushes the slit disc 42 away from the shoulder 52 (i.e., the valve seat) of the male Luer connector 46 and into the enlarged chamber 44 of the male Luer lock connector 46.

By the force of gravity, liquid is urged out of the IV bag, through the tubing of the IV set, and into the enlarged chamber 44 of the male Luer connector 46. Any air within the tubing is also urged through the tube and into the chamber 44 of the male Luer connector 46. The liquid and air within the chamber 44 then travel past the tilted disc 42, through the chamber 40 of the connector 46, and into the passageway 20 of the end cap assembly 14. The air passes through the hydrophobic filter vent 19, while the liquid remains in the passageway 20 of the end cap assembly 14. At this point, the IV set is self-primed and free of air.

Once the air is purged from the IV set, the cap assembly 14 is removed from the male Luer connector 46, and the disc 42 comes to rest against the shoulder 52 of the male Luer connector 46 (as shown in FIG. 2B). The distal end of the male Luer connector 46 is then either directly or indirectly connected to a catheter that is intravenously connected to a patient. The liquid from the IV bag is then delivered under pressure through the IV set by an infusion pump that is connected to the IV set. The pressurized liquid causes the radial slits 43 of the valve 42 to open, and the liquid is expelled from the male Luer connector 46 and is ultimately distributed intravenously to the patient by the catheter.

Figure 3A:
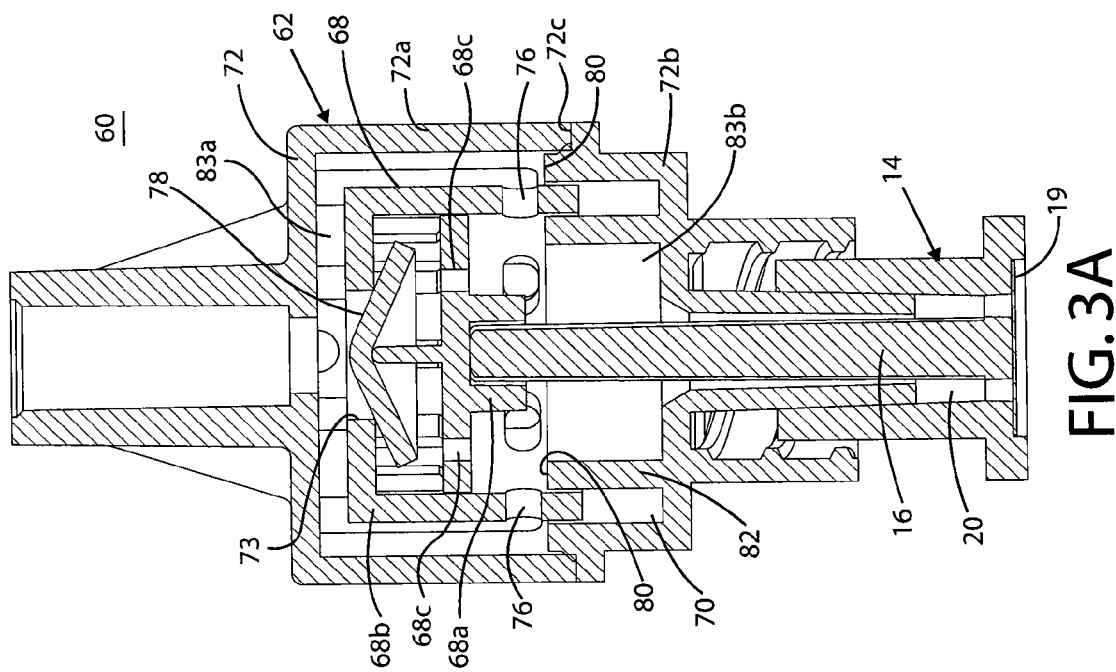
FIG. 3A depicts a cross-sectional side elevation view of yet another IV set valve according to a third exemplary embodiment of the invention.

FIG. 3A depicts a cross-sectional side elevation view of yet another IV set valve 60 according to a third exemplary embodiment of the invention. The IV set valve 60 generally includes a male Luer connector 62 (shown by itself in FIG. 3B) and the previously-described end cap assembly 14. The IV set valve 60 is substantially similar to the IV set valve 40 of FIG. 2A, and only the primary differences between those valves will be described hereinafter.

The housing 72 of the male Luer connector 62 includes two portions 72a and 72b that are fixed to each other at interface 72c by either an adhesive or an ultrasonic weld, for example. A two-piece cage 68 is movably positioned in an annular recess 70 that is defined by opposing cylindrical walls of the housing portion 72b of the male Luer connector 62. The cage 68 translates in a vertical fashion within the annular recess 70. The cage 68 includes a central cage part 68a and a cup-shaped cage part 68b.

The central cage part 68a includes a central recess on its bottom end in which the free end of the actuator 16 is movably positioned. The central cage part 68a also includes a series of openings 68c through which liquid and gas may pass, as will be described later.

The cup-shaped cage part 68b includes a series of openings 76. The opening 76 are provided in a side wall of the cup-shaped cage part 68b through which liquid and gas may pass. The openings 76 register with the surface 80 of the interior cylindrical wall 82 to either permit or prevent the passage of fluid through the openings 76. More particularly, when the openings 76 are positioned at an elevation above the surface 80, as shown, fluid can pass through the openings 76. In contrast, when the openings 76 are positioned at an elevation below the surface 80, as shown in FIG. 3B, fluid can not pass through the openings 76.

A deformable disc 78 is mounted to an opening 73 that is defined on the top surface of the cage part 68b. Although not shown, the disc 78 deforms when it is exposed to pressurized fluid, thereby permitting liquid and gas to flow over the top surface of the deformed disc 78 and through the opening 73. The disc 78 returns to its original shape in the absence of pressure. The deformable disc 78 may also be referred to herein as a valve, a valve element, or a seal.

As shown in FIG. 3A, when the end cap assembly 14 is fitted onto the male Luer connector 62, the free end of the actuator 16 bears on the central cage part 68a and translates the entire cage 68 in an upward direction. After the cage 68 has translated a pre-determined amount, the openings 76 in the cage 68 rise above the top surface 80 of the wall 82. Once the openings 76 are exposed, liquid and gas may pass through the openings 76 and into the chamber 83b.

To prime an IV set including the valve 60, the IV set is fluidly connected to the IV bag (not shown). The end cap assembly 14 is fitted onto the distal end of the male Luer connector 62. As the end cap assembly 14 is fitted onto the male Luer connector 62, the free end of the actuator 16 pushes the cage 68 upwards such that the openings 76 rise above the top surface 80 of the wall 82, as shown in FIG. 3A.

By the force of gravity, liquid is urged out of the IV bag, through the tubing of the IV set, and into the chamber 83a of the male Luer connector 62. Any air within the tubing is also urged through the tube and into the chamber 83a of the male Luer connector 62. The liquid and air within the chamber 83a then travel between the cage 68 and the housing portion 72a, and enter the openings 76 of the cage 68. The liquid and air collect in the chamber 83b of the housing portion 72b and ultimately enter the passageway 20 of the end cap assembly 14 under gravity. The air passes through the hydrophobic filter 19, while the liquid remains in the passageway 20 above the hydrophobic filter 19. At this point, the IV set is self-primed and free of air.

Once the air is purged from the IV set, the end cap assembly 14 is removed from the male Luer connector 62, and the cage 68 translates downward such that the openings 76 of the cage 68 are concealed within the annular recess 70. The distal end of the male Luer connector 62 is then either directly or indirectly connected to a catheter that is intravenously connected to a patient. The liquid from the IV bag is then delivered under pressure through the IV set by an infusion pump that is connected to the IV set. The pressurized liquid causes the disc 78 to deform (deformation not shown) and the liquid flows over the deformed top surface (not shown) of the disc 78 and through the opening 73 in the cage part 68b. The liquid then flows through the openings 68c in the cage part 68a and into the chamber 83b of the housing portion 72b. The liquid is expelled from the male Luer connector 62 through the frustoconical portion 17 and is ultimately distributed intravenously to the patient by the catheter (not shown) that is connected to the connector 62. The disc 78 returns to its natural position shown in FIG. 3B in the absence of pressure.

FIG. 4A depicts a cross-sectional side elevation view of still another IV set valve 90 according to a fourth exemplary embodiment of the invention. The IV set valve 90 generally includes a male Luer connector 92 (shown by itself in FIG. 4B) and the previously-described end cap assembly 14. The IV set valve 90 is substantially similar to the IV set valve 40 of FIG. 2A, and only the primary differences between those valves will be described hereinafter.

The male Luer connector 92 includes a housing 91 that is comprised of an upper housing portion 91a that is fixedly mounted to a lower housing portion 91b at interface 91c. A series of flow channels 102 are provided on the interior side wall of the housing 91. The flow channels 102 are defined between adjacent ribs 99 that are provided on surfaces of the upper housing portion 91a.

A chamber 103 is defined in the housing 91 in which a seal 93 is moveably positioned. The seal 93 can translate between a lower elevation where its lower surface contacts a bottom surface 98 (otherwise referred to as a valve seat) of the chamber 103, and a higher elevation where the upper surface of the seal 93 contacts the ribs 99.

As shown in FIG. 4B, when the seal 93 is positioned against the bottom surface 98 of the chamber 103, the seal 93 prevents the inadvertent passage of liquid and gas into the chamber 105. However, when the seal 93 is separated from the bottom surface 98 of the lower housing portion 91b, the seal 93 permits the passage of liquid and gas into the chamber 105. The seal 93 may also be referred to herein as a valve or a valve element.

The seal 93 includes a flexible upper seal member 95 that is fixedly mounted to a rigid support member 96 that is optionally composed of plastic. A slit 97 is defined on the flexible seal member 95. Although not shown, the slit 97 opens when it is exposed to pressurized fluid, thereby permitting liquid and gas to flow through the slit 97 of the seal 93. As shown in FIG. 4B, the rigid plastic support member 96 of the seal 93 includes an outer portion 96b, a central portion 96c, and one or more openings 96d that are defined between those portions 96b and 96c. The openings 96d provide a passage through which liquid and gas may flow into the chamber 105.

To prime an IV set including the valve 90, the proximal end 92a of the connector 92 is connected to one end of the IV set, and the other end of the IV set is fluidly connected to the IV bag (not shown). The end cap assembly 14 is fitted onto the distal end of the male Luer connector 92. As the end cap assembly 14 is fitted onto the male Luer connector 92, the actuator 16 pushes the seal 93 upwards thereby separating the seal 93 from the bottom surface 98 of the lower housing portion 91b.

By the force of gravity, liquid is urged out of the IV bag, through the tubing of the IV set, and into the chamber 103 of the male Luer connector 92. Any air within the tubing is also urged through the tube and into the chamber 103 of the male Luer connector 92. The liquid and air within the chamber 103 then travel through the gap (see FIG. 4A) between the bottom end of the seal 93 and the bottom surface 98 of the lower housing portion 91b. The liquid and air collect in the chamber 105 defined by the frustoconical portion of the Luer connector and ultimately enter the passageway 20 of the end cap assembly 14. The air passes through the hydrophobic filter vent 19, while the liquid remains in the passageway 20 of the end cap assembly 14 above the hydrophobic filter vent 19. At this point, the IV set is self-primed and free of air.

Once the air is purged from the IV set, the end cap assembly 14 is removed from the male Luer connector 92, and the seal 93 translates downward such that the bottom end of the seal 93 re-seats on the bottom surface 98 of the lower housing portion 91b. The distal end 92b of the male Luer connector 92 is then either directly or indirectly connected to a catheter (not shown) that is intravenously connected to a patient. The liquid from the IV bag is then delivered under pressure through the IV set by an infusion pump that is connected to the IV set. The pressurized liquid causes the slit 97 of the seal 93 to open and the liquid flows through the slit 97, through the openings 96d of the support member 96, and the liquid is expelled from the male Luer connector 92 and is ultimately distributed intravenously to the patient by the catheter (not shown) that is connected to the connector 92. The slit 97 of the seal 93 returns to its natural position shown in FIG. 4A in the absence of pressure.

FIG. 5A depicts a cross-sectional side elevation view of still another IV set valve 110 according to a fifth exemplary embodiment of the invention. The IV set valve 110 generally includes a male Luer connector 112 (shown by itself in FIG. 5B) and an end cap assembly 114. The IV set valve 110 is substantially similar to the IV set valve 60 of FIG. 3A, and only the primary differences between those valves will be described hereinafter.

The male Luer connector 112 includes a housing 116 that is comprised of a top housing portion 116a that is fixedly mounted to a lower housing portion 116b at interface 116c. A series of flow channels 118 are provided on the interior side wall of the housing 116a through which fluid may pass.

A spring-loaded piston 120 is moveably positioned within a chamber 122 of the lower housing part 116b. A series of openings 120a are provided in the piston 120, through which fluid may pass. A threaded aperture 120b is defined on the lower surface of the piston 120.

A moveable seal 121 is positioned above the spring-loaded piston 120. The moveable seal 121 moves between a floating position (see FIG. 5A) and a seated position (see FIG. 5B). In the floating position, the seal 121 is surrounded by ribs 119 that project from the interior surface of the upper housing part 116a. A series of openings 118 are defined between adjacent ribs 119 so that fluid may pass over the surface of the seal 121 and through the openings 118. In the seated position of the seal 121, the top surface of the seal 121 is seated against a valve seat 130 that is formed on the upper housing part 116a.

The piston 120 can translate between a lower elevation where it contacts a bottom surface 127 (see FIG. 5B) of the chamber 122, and a higher elevation where the top end of the piston 120 contacts and deforms the seal 121, as shown in FIG. 5B.

As shown in FIG. 5B, when the seal 121 is positioned against the valve seat 130, the seal 121 prevents the inadvertent passage of liquid and gas into the chamber 122 of the connector 112. However, when the seal 121 is separated from the valve seat 130, as shown in FIG. 5A, the seal 121 permits the passage of liquid and gas into the chamber 122 via the openings 118. The seal 121 may also be referred to herein as a valve or a valve element.

The end cap assembly 114 is similar to the end cap assembly 14 with various exceptions. The end 134 of the actuator 132 is threaded so that it can engage the threaded aperture 120b of the piston 120. A series of openings 136 are provided at the base of the actuator 132 to permit the passage of fluid. A hydrophobic filter vent 138 is mounted to the bottom end of the end cap assembly 114 at an elevation below the openings 136.

To prime an IV set including the valve 110, one end of the IV set is connected to the proximal end 112a of the connector 112 and the other end of the IV set is fluidly connected to the IV bag (not shown). The end cap assembly 114 is fitted onto the distal end 112b of the male Luer connector 112. As the end cap assembly 114 is threaded onto the shroud 64 of the male Luer connector 112, the threaded end 134 of the actuator 132 simultaneously engages the threaded aperture 120b of the piston 120, thereby pulling the spring loaded piston 120 in a downward direction (see FIG. 5A). The seal 121 then separates from the valve seat 130 by gravity.

As depicted by the arrows in FIG. 5A, by the force of gravity, liquid is urged out of the IV bag, through the tubing of the IV set, and into the chamber 140 of the male Luer connector 112. Any air within the tubing is also urged through the tube and into the chamber 140 of the male Luer connector 112. The liquid and air within the chamber 140 then travel past the seal 121, through the openings 118 formed in the upper housing part 116a, through the openings 120a of the piston 120, through the annular fluid passageway 150 that is formed around the actuator 132, through the openings 136 formed at the base of the actuator 132. The air passes through the hydrophobic filter vent 138, while the liquid remains in the openings 136 and the fluid passageway 150. At this point, the IV set is self-primed and free of air.

Once the air is purged from the IV set, the end cap assembly 114 is removed from the male Luer connector 112, and the spring loaded piston 120 moves upward and urges the seal 121 against the valve seat 130, as shown in FIG. 5B. The distal end 112b of the male Luer connector 112 is then either directly or indirectly connected to a catheter (not shown) that is intravenously connected to a patient. The liquid from the IV bag is then delivered under pressure through the IV set by an infusion pump that is connected to the IV set. The pressurized liquid causes the edges of the seal 121 to separate from the valve seat 130. The pressurized liquid then flows over the seal 121, through the openings 120a of the piston 120, through the fluid passageway 150, and the liquid is expelled from the male Luer connector 112 and is ultimately distributed intravenously to the patient by the catheter (not shown) that is connected to the connector 112. The seal 121 returns to its natural position shown in FIG. 5B in the absence of pressure.

Figure 7:
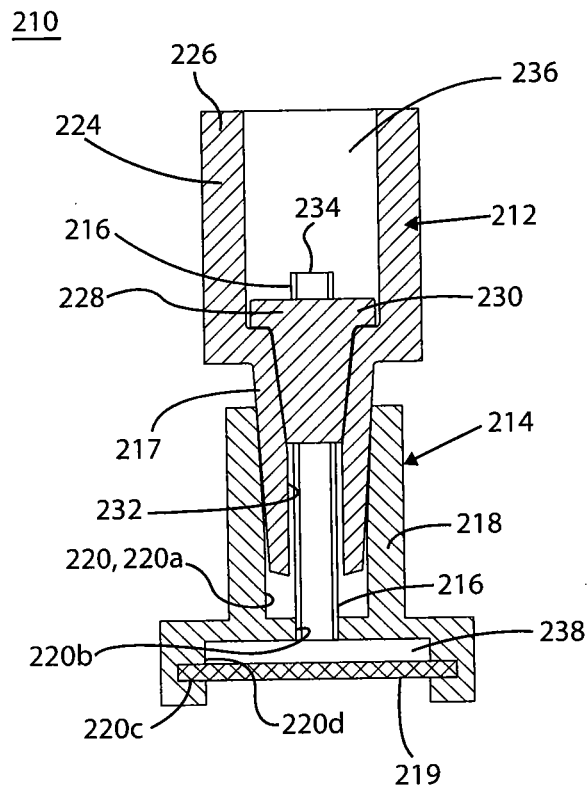
FIG. 7 depicts a cross-sectional side elevation view of still another IV set valve including a vented end cap assembly that is releasably mounted to a connector according to a sixth exemplary embodiment of the invention.

FIG. 7 depicts a cross-sectional side elevation view of still another IV set valve 210 according to a sixth exemplary embodiment of the invention. The IV set valve 210 includes a connector 212 and a vented end cap assembly 214 that is releasably mounted to the connector 212. The IV set valve 210 may or may not be permanently mounted to an IV set (not shown).

The end cap assembly 214 is friction fitted onto the frustoconical portion 217 of the male Luer connector 212. Although not shown, the male Luer connector 212 may include a shroud (like shroud 64 of FIG. 1A) having female threads that surrounds the frustoconical portion 217 of the male Luer connector 212 for coupling with a female Luer connector (not shown). If the male Luer connector 212 includes such a threaded shroud, then the end cap assembly 214 may optionally include a male Luer thread for threadedly mating with the female threads of the threaded shroud of the male Luer connector 212.

Referring now to the components of the end cap assembly 214, the end cap assembly 214 generally includes a body portion 218 defining a stepped bore 220, a hydrophobic filter vent 219 that is non-removably mounted in the stepped bore 220, and an actuator tube 216 that is non-removably mounted in the stepped bore 220 and is positioned to extend in an upward direction toward the male Luer connector 212. The cap assembly 214 may or may not be coated with a hydrophobic substance and or an antimicrobial compound. The cap assembly 214 may or may not be pre-mounted onto the distal end of the connector 212.

The body portion 218 has a hollow revolved body that is composed of either a plastic or a metallic material. The stepped bore 220 has four portions 220a-220d. The portion 220a is sized to receive the frustoconical end 217 of the male Luer connector 212. The portion 220b is sized to receive the actuator tube 216. The portion 220c is sized to receive the hydrophobic filter vent 219. The portion 220d defines the chamber 238 in which the pooled fluid collects.

The actuator tube 216 is a hollow tube that is open at both ends. The actuator tube 216 is composed of either a plastic or a metallic material. The actuator tube 216 may be insert molded with the body portion 218. Alternatively, the actuator tube 216 may be mounted to the body portion 218 by an adhesive or an ultrasonic weld, for example.

Turning now to the features of the male Luer connector 212, the male Luer connector 212 includes a hollow body 224 including a tubular shaped proximal end 226 and the frustoconical portion 217 that extends in a distal direction. The tubular shaped proximal end 226 has a hollow chamber 236 in which fluid from the IV bag can collect. A valve element 228 is seated on a shoulder 230 (otherwise referred to as a valve seat) of the tubular portion 226 and extends into a recess 232 that is defined in the frustoconical portion 217 of the Luer connector 212. The valve element 228 may also be referred to herein as a valve, a valve element, a duckbill valve, or a seal.

The duckbill valve 228 is biased toward a closed position, and, in the absence of pressure or the actuator tube 216, the duckbill valve 228 prevents the passage of gases and liquid there through. In the presence of either the actuator tube 216 or pressurized fluid produced by gravity or an infusion pump, the duckbill valve 228 opens (open configuration not shown) to permit the passage of gases and liquid there through. The duckbill valve 228 is also configured to prevent siphoning of fluid from the IV bag. A duckbill valve is disclosed in U.S. Pat. No. 6,092,551 to Bennett, which is incorporated by reference herein in its entirety.

To prime an IV set including the valve 210, one end of the IV set is connected to the proximal end of the valve 210, the and the other end of the IV set is fluidly connected to the IV bag (not shown). The end cap assembly 214 is fitted onto the frustoconical portion 217 of the male Luer connector 212 of the valve 210 for self-priming purposes.

As the end cap assembly 214 is fitted onto the male Luer connector 212, the actuator tube 216 penetrates the opening (not shown) provided on the bottom end of the duckbill valve 228. Once the end cap assembly 214 is fitted onto the male Luer connector 212, the top open end 234 of the actuator tube 216 resides above the duckbill valve 228 and is positioned in the chamber 236 of the male Luer connector 212. The actuator tube 216 fluidly connects the chamber 236 of the tubular portion 226 of the male Luer connector 212 with the chamber 238 of the end cap assembly 214.

By the force of gravity, fluid within the IV set travels through the tubing of the IV set, and into the chamber 236 of the male Luer connector 212. Any air within the tubing is also urged through the tube and into the chamber 236 of the male Luer connector 212. The liquid and air within the chamber 236 then travel through the exposed open end 234 of the actuator tube 216, through the actuator tube 216 and into the chamber 238 of the end cap assembly 214 that is delimited by the hydrophobic filter vent 219. The fluid then collects on the hydrophobic filter vent 219. The air passes through the hydrophobic filter vent 219, while the liquid remains above the hydrophobic filter vent 219 in the chamber 238. At this point, the IV set is self-primed and free of air.

Once the air is purged from the IV set, the cap assembly 214 is removed from the male Luer connector 212. The duckbill valve 228 returns to a closed position once the actuator tube 216 is removed from the Luer connector 212. The distal end of the male Luer connector 212 is then either directly or indirectly connected to a catheter that is connected to a patient's vascular system. The liquid from the IV bag is then delivered under pressure through the IV set by an infusion pump that is connected to the IV set. The pressurized liquid causes the duckbill valve 228 to open, and the liquid is expelled from the male Luer connector 212 and is ultimately distributed intravenously to the patient by the catheter.

While preferred embodiments of the invention have been described herein, it will be understood that such embodiments are provided by way of example only. Numerous variations, changes and substitutions will occur to those skilled in the art without departing from the spirit of the invention. It is intended that the appended claims cover all such variations as fall within the spirit and scope of the invention.

What is claimed:

1. A self-priming IV set valve comprising:
  a connector including a hollow body, a frustoconical portion extending away from the body, and a valve element located in a chamber defined by the body and the frustoconical portion; and
  a cap that is configured to encompass and be removably connected to an outer surface of the frustoconical portion of the connector, said cap including a hydrophobic filter and an actuator extending in a direction away from the hydrophobic filter and toward the valve element, the hydrophobic filter being configured to permit the passage of air but not liquid;
  wherein, when the cap is mounted to the connector, the actuator extends through the frustoconical portion of the connector and engages the valve element to form a passageway in the connector such that air and liquid are permitted to pass through the connector and into the cap whereupon the hydrophobic filter of the cap prevents the passage of liquid through the hydrophobic filter while the hydrophobic filter permits the passage of air out of the cap and into the atmosphere, and,
  wherein, when the cap is not mounted to the connector, the valve element of the connector is configured to open under pressure to permit the passage of liquid through the connector and close when pressure ceases.

2. The valve of claim 1, wherein the actuator is configured to puncture the valve element.

3. The valve of claim 1, wherein the actuator includes an opening that forms at least portion of the passageway such that air and liquid are permitted to pass over or through the valve element, into the opening of the actuator and onto the hydrophobic filter.

4. The valve of claim 1, wherein the actuator includes a recessed portion that extends from a tip of the actuator that forms at least part of the passageway when the cap is connected to the connector.

5. The valve of claim 1, wherein the actuator is sized to move the valve element upon connecting the cap to the connector.

6. The valve of claim 1, wherein the connector is a male Luer connector.

7. The valve of claim 1, wherein a fluid passageway is defined between an outer surface of the actuator and an inner surface of the frustoconical portion of the cap.

8. The valve of claim 1, wherein the connector includes a movable cage and the valve element is mounted to the moveable cage,
  wherein, upon connecting the cap to the connector, the actuator of the cap moves the cage to expose a portion of the fluid passageway without deforming the valve element.

9. The valve of claim 8, wherein the movable cage includes an opening that registers with a wall of the connector, wherein upon connecting the cap to the connector, the opening is spaced from the wall such that the opening forms said portion of the fluid passageway and air and liquid can travel through the opening and into the cap, and when the cap is not connected to the connector, the opening is positioned adjacent to the wall of the cage such that air and liquid can not travel through the opening of the cage and into the cap.

10. A self-priming IV set valve comprising:
a connector including a valve element that is at least partially positioned inside of the connector; and
a cap that is configured to be removably connected to the connector, said cap including a hydrophobic filter that is configured to permit the passage of air but not liquid;
wherein, when the cap is mounted to the connector, a passageway is formed in the connector such that air and liquid are permitted to pass through the connector and into the cap whereupon the hydrophobic filter of the cap prevents the passage of liquid through the hydrophobic filter while the hydrophobic filter permits the passage of air out of the cap and into the atmosphere,
wherein, when the cap is not mounted to the connector, the valve element of the connector is configured to open under pressure to permit the passage of liquid through the connector and close when pressure ceases,
wherein the connector includes a movable cage and the valve element is mounted to the moveable cage,
wherein, upon connecting the cap to the connector, the actuator of the cap moves the cage to expose a portion of the fluid passageway without deforming the valve element
wherein the cap includes an actuator that is configured to either open or move the valve element to form the passageway such that air and liquid are permitted to pass through the connector and into the cap, and
wherein the movable cage includes an opening that registers with a wall of the connector, wherein upon connecting the cap to the connector, the opening is spaced from the wall such that the opening forms said portion of the fluid passageway and air and liquid can travel through the opening and into the cap, and when the cap is not connected to the connector, the opening is positioned adjacent to the wall of the cage such that air and liquid can not travel through the opening of the cage and into the cap.

11. The valve of claim 10, wherein the actuator is configured to puncture the valve element.

12. The valve of claim 10, wherein the actuator includes an opening that forms at least portion of the passageway such that air and liquid are permitted to pass over or through the valve element, into the opening of the actuator and onto the hydrophobic filter.

13. The valve of claim 10, wherein, when the cap is connected to the connector, one end of the actuator is positioned adjacent the hydrophobic filter, and the other end of the actuator is positioned within an interior of the connector.

14. The valve of claim 10, wherein the actuator includes a recessed portion that extends from a tip of the actuator that forms at least part of the passageway when the cap is connected to the connector.

15. The valve of claim 10, wherein the actuator is sized to move the valve element upon connecting the cap to the connector.

16. The valve of claim 10, wherein the connector is a male Luer connector.

17. The valve of claim 10, wherein the actuator is connected to the cap and spaced from the hydrophobic filter.

* * * * *